US00PP13124P2

(12) United States Plant Patent
Heims

(10) Patent No.: US PP13,124 P2
(45) Date of Patent: Oct. 22, 2002

(54) PULMONARIA PLANT NAMED 'NORTHERN LIGHTS'

(75) Inventor: Daniel M. Heims, Tigard, OR (US)

(73) Assignee: Terra Nova Nurseries, Inc., Tigard, OR (US)

( * ) Notice: Subject to any disclaimer, the term of this patent is extended or adjusted under 35 U.S.C. 154(b) by 0 days.

(21) Appl. No.: 09/894,588

(22) Filed: Jun. 28, 2001

(51) Int. Cl.[7] ..... A01H 5/00
(52) U.S. Cl. ..... Plt./263
(58) Field of Search ..... Plt./263

*Primary Examiner*—Bruce R. Campell
*Assistant Examiner*—Annette H. Para
(74) *Attorney, Agent, or Firm*—Klarquist Sparkman, LLP

(57) ABSTRACT

A new and distinct hybrid of Pulmonaria plant characterized by silver foliage and pink flowers.

2 Drawing Sheets

BOTANICAL CLASSIFICATION

Pulmonaria hybrid.

VARIETY DENOMINATION

'Northern Lights'.

The present invention relates to a new and distinct hybrid of Pulmonaria, of the family Boraginaceae, which originated as an open-pollinated cross between unknown parents. This is known to be an outcross because Pulmonaria does not normally self-pollinate. Due to the fact that the instant plant and parent plants are interspecific hybrids from several generations of interbreeding and selecting, no species designations are given.

The new variety has been reproduced only by asexual propagation (division and tissue culture). Each of the progeny exhibits identical characteristics to the original plant.

This plant is characterized by the following:

1. Very silver foliage with deeply undulating margins.
2. Pink flowers.

Asexual propagation by division and tissue culture as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

DETAILED PLANT DESCRIPTION

Figure 1:
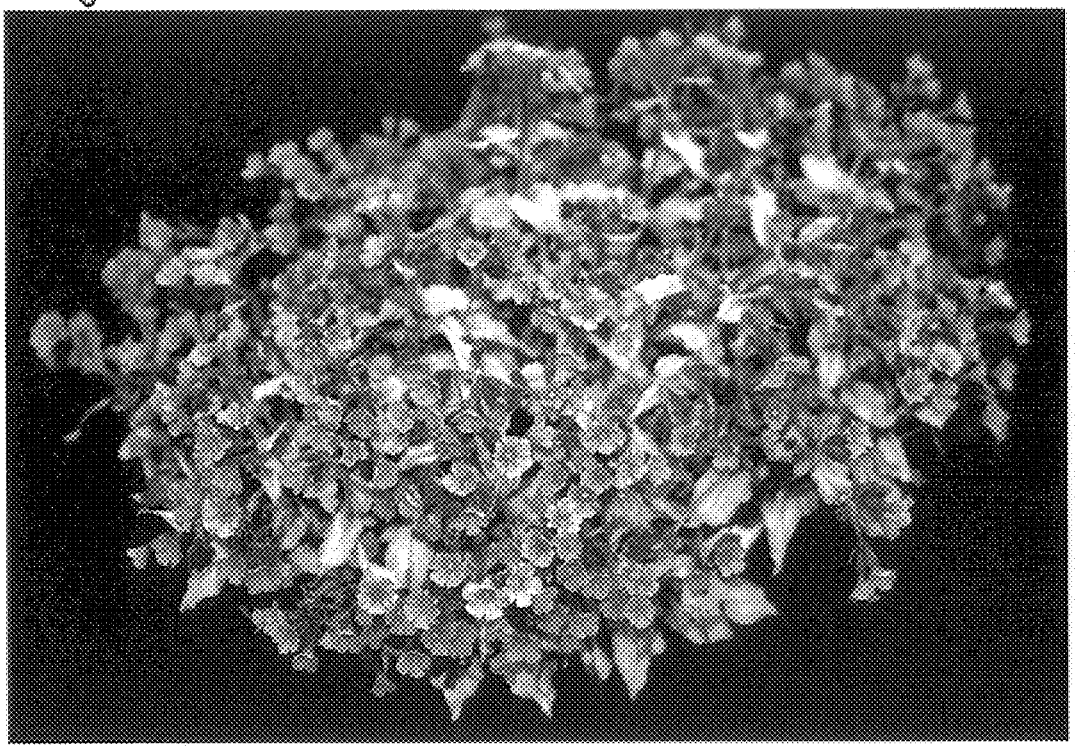
FIG. 1 shows Pulmonaria 'Northern Lights' in flower in the spring.
Figure 2:
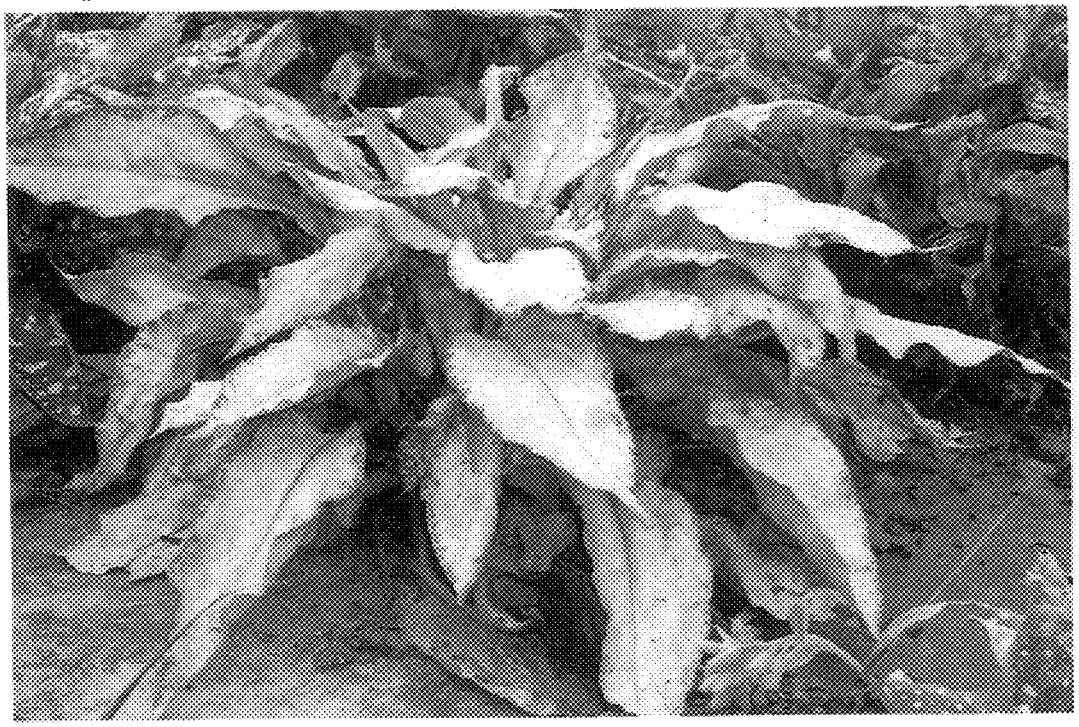
FIG. 2 shows the foliage in the field in June in Canby, Oreg.

The following is a detailed description of the new Pulmonaria hybrid based on observations of a one-year old specimen grown in the trial field in Canby, Oreg. The color descriptions are all based on The Royal Horticultural Society Colour Chart.

Plant:
- *Type*.—Herbaceous perennial.
- *Hardiness*.—USDA Zones 4 to 5.
- *Spring size*.—32 cm. wide and 20 cm. tall when first flowering.
- *Summer size*.—50 cm. wide and 37 cm. tall.
- *Form*.—Basal clump.

Leaf:
- *Type*.—Simple.
- *Shape*.—Ovate to Elliptic.
- *Arrangement*.—Rosette.
- *Length*.—45 cm.
- *Width*.—9 cm.
- *Petiole length*.—14 to 16 cm.
- *Margins*.—Entire, undulating in large waves.
- *Apex*.—Acuminate.
- *Base*.—Attenuate.
- *Leaf texture*.—Scabrous.
- *Petiole texture*.—Scabrous.
- *Petiole color*.—Yellow Green 148C.
- *Venation*.—Reticulate.
- *Color*.—Topside — Silver, Closest to 196D with Green 137A on edges. Bottom — Yellow Green 146C.

Cauline leaves (found in the spring only on the flowering stems):
- *Type*.—Simple.
- *Arrangement*.—Alternate.
- *Shape*.—Oblanceolate near bottom of the stem and elliptic near the top.
- *Length*.—5 to 11 cm.
- *Width*.—2.2 cm.
- *Margins*.—Entire. Somewhat revolute, undulating.
- *Apex*.—Acuminate.
- *Base*.—Clasping, sessile.
- *Leaf texture*.—Hirsute.
- *Venation*.—Pinnate.
- *Color*.—Topside: Silver, closest to Greyed-Green 194B with darker edge Greyed Orange 166A. Bottom side: Yellow Green 146C.

Inflorescence:
- *Type*.—Terminal forked cyme.
- *Peduncle*.—Height: 25 cm. Diameter: 0.35 cm. Color: Greyed Purple 184A overlaying Yellow Green 145C. Texture: Hirsute.

*Pedicel*.—Length: Varies. Grows to 1.4 cm. Texture: Hirsute. Color: Greyed Orange 177A.

Flower bud:

*Size*.—1.7 cm. long and 0.7 cm. wide.

*Shape*.—Ovoid.

*Color*.—Rose pink. Red Group 53C.

Flower:

*Type*.—Actinomorphic.

*Shape*.—Funnelform.

*Size*.—1.8 cm deep and 1.3 cm. wide.

*Corolla*.—5 fused petals with rounded lobes.

*Color*.—Pink. Red 54A with darker throat when fully open. Varies from youngest flower, Purple Violet 81B with pink throat to Red 54A to oldest flower, Violet 87A.

*Calyx*.—5 fused sepals, tubular campanulate, parted ⅓ to base, hirsute and with glandular hairs, 1.6 cm. deep.

*Calyx color*.—Greyed Orange 177A.

*Pistil*.—Short, 0.6 cm., thrum type, Yellow Green 145A.

*Ovary position:*.—Partly inferior.

*Carpel number*.—4.

*Stamen number*.—5, in the tube.

*Pollen color*.—White 155A.

*Bloom period*.—Late February to late April in Canby, Oreg.

*Fragrance*.—None.

Seed:

*Type*.—4 smooth nutlets, Black 202A and shiny, typical of the genus.

*Fertility*.—Fertile.

Disease: None observed on plant grown under commerical conditions in Canby, Oreg.

COMPARISONS TO SIMILAR PULMONARIA

Compared to Pulmonaria 'Excalibur' (U.S. Plant Pat. No. 8,958), the instant plant has more silvering on the leaves, larger flowers, and a pink flower color.

Compared to Pulmonaria 'High Contrast' (U.S. Plant patent application Ser. No. 09/628,782), the instant plant has pinker flowers, more silvering on its leaves, and a more undulating leaf.

Compared to Pulmonaria 'Silver Streamers' (U.S. Plant patent application Ser. No. 09/324,625), the instant plant has pinker flowers, bigger, more robust foliage, and margins that undulate deep into the leaf rather than many shallow undulations along the margin.

I claim:

1. A new and distinct hybrid of Pulmonaria plant substantially as shown and described, characterized by a combination of silver foliage and pink flowers.

* * * * *